(12) United States Patent
Warila

(10) Patent No.: US 7,727,284 B2
(45) Date of Patent: Jun. 1, 2010

(54) PROSTHETIC SUSPENSION DEVICE

(76) Inventor: Jeffery W. Warila, 94 N. Hayden Bay Dr., Portland, OR (US) 97217

( * ) Notice: Subject to any disclaimer, the term of this patent is extended or adjusted under 35 U.S.C. 154(b) by 1477 days.

(21) Appl. No.: 11/083,840

(22) Filed: Mar. 16, 2005

(65) Prior Publication Data

US 2005/0209706 A1 Sep. 22, 2005

Related U.S. Application Data

(60) Provisional application No. 60/554,304, filed on Mar. 17, 2004.

(51) Int. Cl.
*A61F 2/78* (2006.01)
*A61F 2/80* (2006.01)

(52) U.S. Cl. .......................... 623/36; 623/33

(58) Field of Classification Search ........................ None
See application file for complete search history.

(56) References Cited

U.S. PATENT DOCUMENTS 6,666,894 B2 * 12/2003 Perkins et al. ................. 623/36
6,793,682 B1   9/2004 Mantelmacher .............. 623/36

FOREIGN PATENT DOCUMENTS

WO  WO 03/041619 A1 * 5/2003

OTHER PUBLICATIONS

Alpha Locking Lanyard Fabrication Instructions, Ohio Willow Wood brochure dated Aug. 11, 2003 (4 pages).*
"Icelock Module", Gudjonsson, Össur, Nov. 2000, 23 pages.
Kahle, Jason T., "Prosthetic Primer: Socket Basics", *inMotion*, vol. 11, No. 5, Sep./Oct. 2001, 4 pages.

* cited by examiner

*Primary Examiner*—David H. Willse
(74) *Attorney, Agent, or Firm*—Kolisch Hartwell, P.C.

(57) ABSTRACT

A prosthetic suspension device having a positioning element, a coupling element, and a friction-reducing element to facilitate movement of the positioning element towards the coupling element. The positioning element is adapted to maneuver an inner socket of a prosthesis into an outer socket of a prosthesis. The coupling element is configured to receive the positioning element and restrict movement thereof.

21 Claims, 3 Drawing Sheets

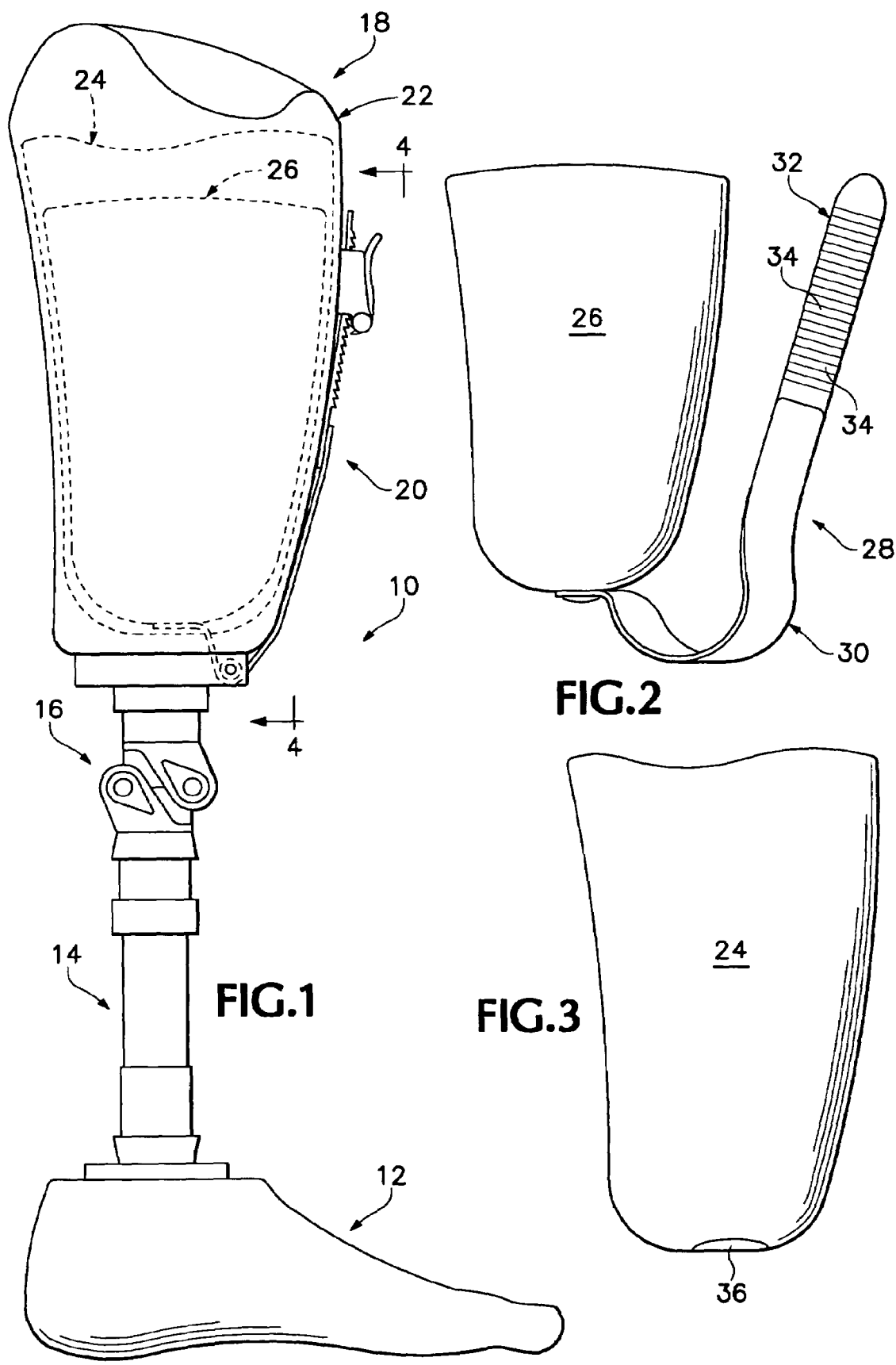

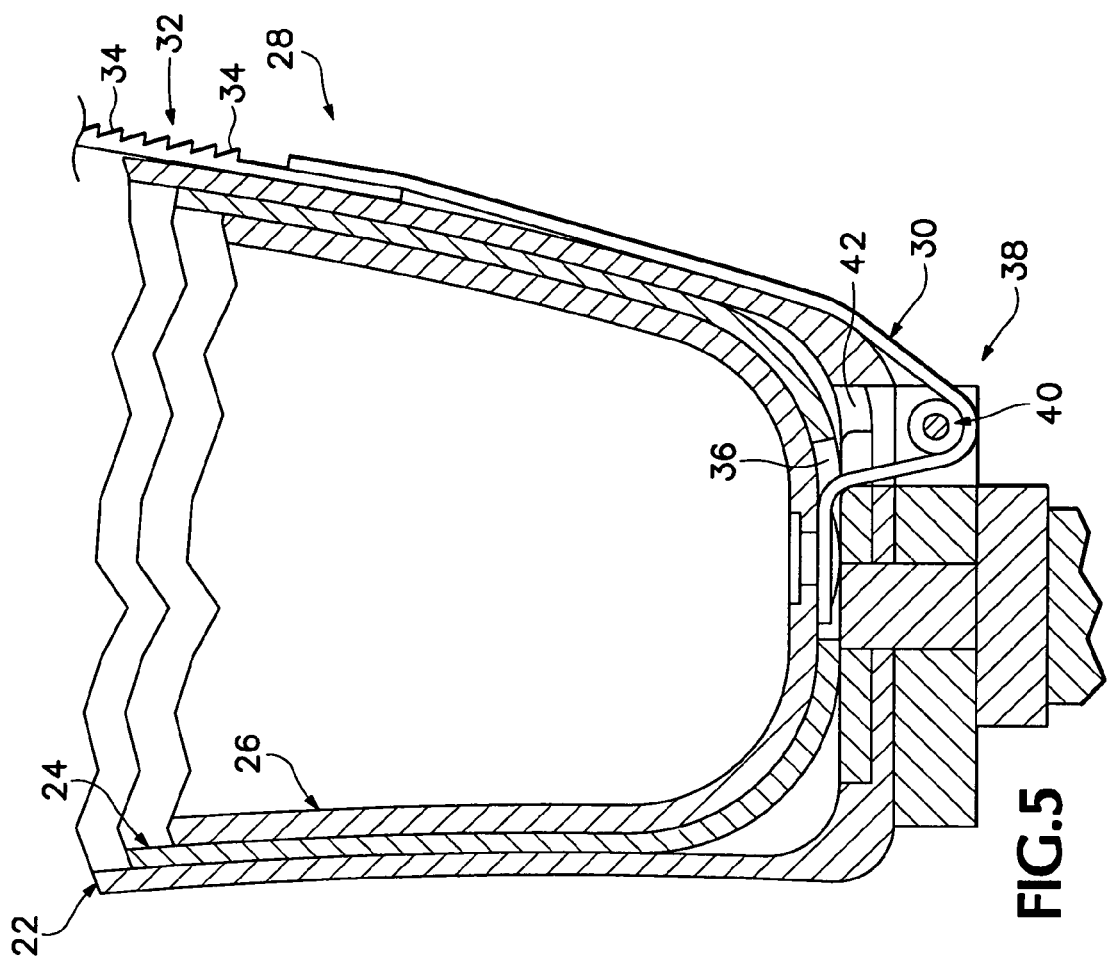
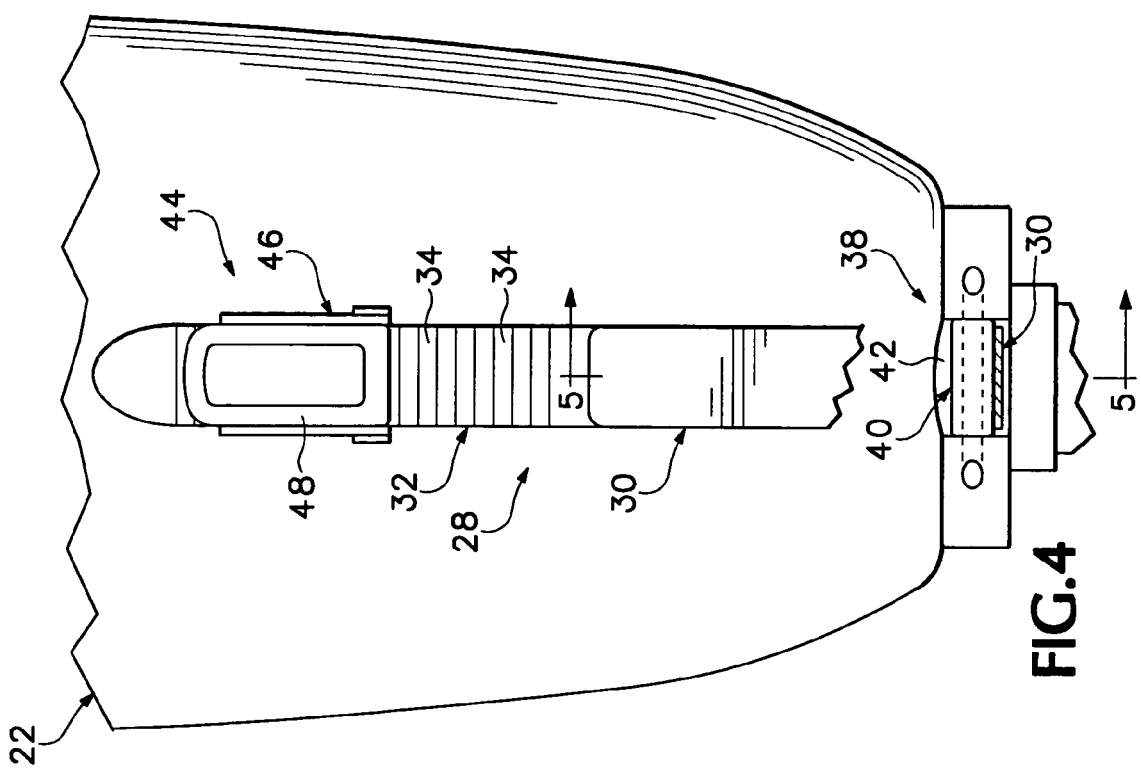

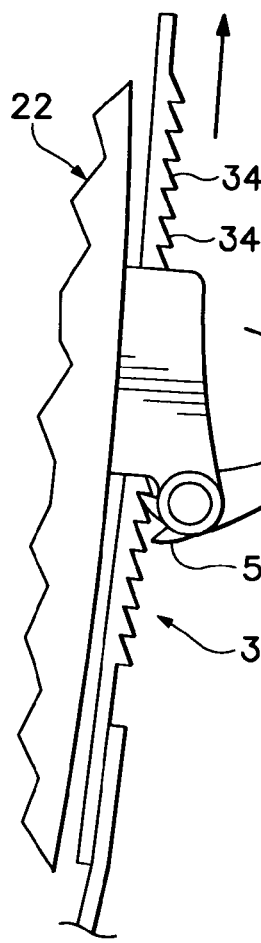
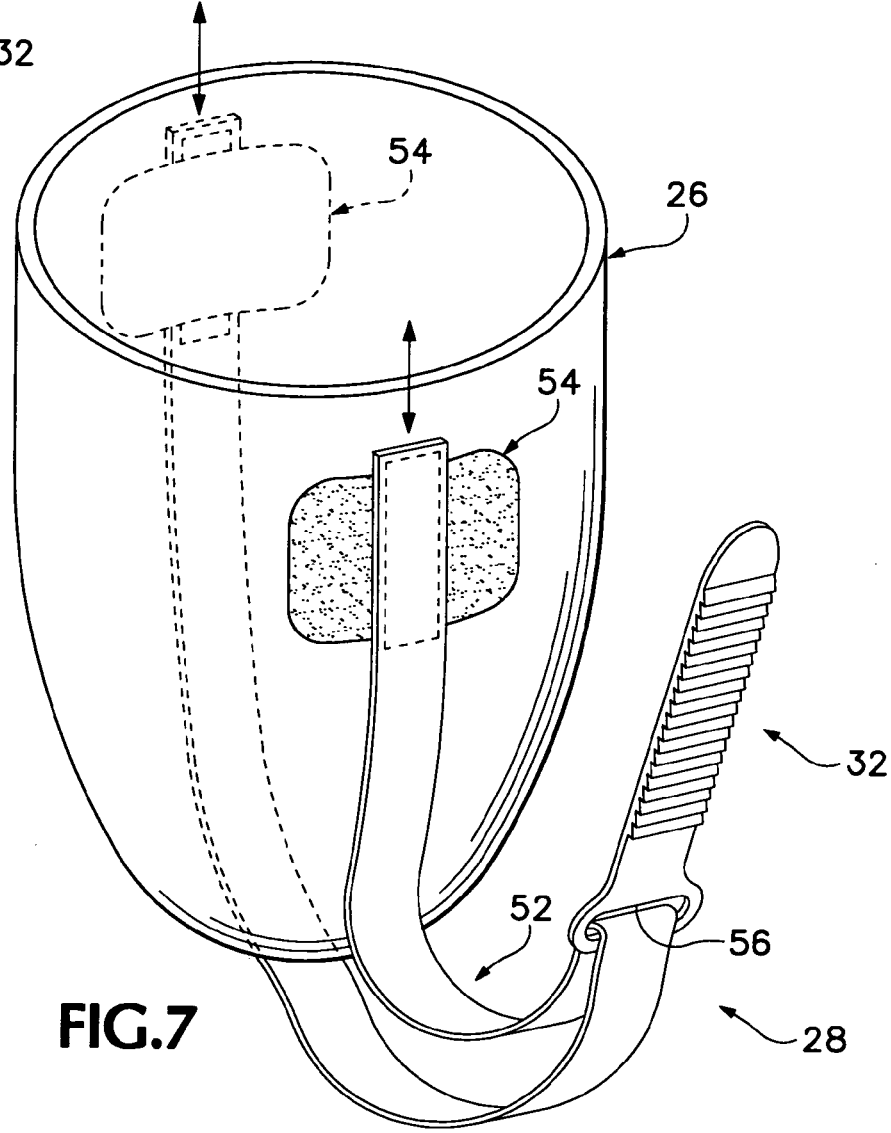

PROSTHETIC SUSPENSION DEVICE

CROSS-REFERENCE TO RELATED APPLICATION

This application claims priority from copending U.S. Patent Application Ser. No. 60/554,304, which was filed on Mar. 17, 2004 and entitled "Prosthetic Distal Attachment Device," the completed disclosure of which is incorporated herein by reference for all purposes.

TECHNICAL FIELD

This disclosure relates generally to prosthetic devices, and more particularly to prosthetic devices for use by lower extremity amputees. The disclosed prosthesis includes a socket assembly having a suspension locking mechanism to assist users in donning the prosthetic device and securing the prosthetic device to a user while the user is physically active.

BACKGROUND OF THE INVENTION

A prosthetic device, or prosthesis, is an artificial substitute for a part of the body such as a limb. Most prostheses have sockets to attach the prosthesis to the amputee's residual limb. One of the challenges of socket design is to maintain a tight fit between the prosthesis and the residual limb, particularly during unweighting of the limb, such as in the swing phase of gait.

Hydrostatic socket designs typically include a gel liner that is placed over the residual limb of the amputee to couple the residual limb to the prosthesis. The prosthesis may include a hard outer socket and a soft intermediate socket that is placed between the gel liner and the hard socket. A bottom or distal attachment device is connected to the liner and engages with the hard socket to secure the prosthesis to the user. The attachment device is commonly a pin, also known as a shuttle lock. Unfortunately, these devices may be difficult for users to properly align since the user may be unable to see the attachment device while trying to engage the attachment device with the rest of the prosthesis. Donning a prosthesis may also be frustrating for older adults and people with diabetes because they often lack upper body strength that is needed to align and secure the sockets to one another. Additionally, these attachment devices require the user to stand during donning so that gravity may be used to align and secure the prosthetic components.

BRIEF DESCRIPTION OF THE DRAWINGS

FIG. 1 shows a side view of an above-the-knee prosthesis having a socket assembly incorporating a suspension device according to the present description.

FIG. 2 illustrates a distal adaptation of a gel liner of the socket assembly of FIG. 1 to include a positioning element having a gripping portion.

FIG. 3 illustrates a soft intermediate socket of the socket assembly of FIG. 1, including an opening through which the positioning element may pass.

FIG. 4 illustrates a front view of a hard outer socket of the prosthesis of FIG. 1, showing the suspension device in the secured position.

FIG. 5 is a cross-sectional view of FIG. 4, showing the positioning element of FIG. 2 passing through an opening in the intermediate and outer sockets and around a friction-reducing element for improved leverage.

FIG. 6 is a side view of the positioning element being inserted into a coupling element which maneuvers and secures the positioning element at a user-defined tension.

FIG. 7 shows another example of an adaptation of a gel liner of the socket assembly of FIG. 1 to include a positioning element having an adjustable gripping portion.

DETAILED DESCRIPTION

The present disclosure provides a suspension device for a lower extremity prosthesis. An embodiment of a prosthesis incorporating the disclosed device is shown in FIG. 1, the prosthesis being indicated generally at 10. As indicated, the prosthesis may be considered to include an artificial foot structure 12, an artificial shin structure 14, an artificial knee structure 16, and a socket assembly 18. In some instances, the prosthesis may further include an artificial ankle structure. The suspension device is shown generally at 20. Although the device shown is incorporated into a prosthesis for above-the-knee amputees, the prosthesis could be modified by removing the artificial knee structure and shifting the socket assembly downward to accommodate a below-the-knee amputee. Further, it will be appreciated that the prosthesis may be covered by artificial skin (not shown) made from a material such as rubber so as to simulate skin.

As shown in FIG. 1, socket assembly 18 may be comprised of a hard outer socket 22 that attaches to the artificial knee structure. It should be appreciated that outer socket 22 may be attached to artificial shin structure 14 for a below-the-knee prosthesis. Outer socket 22 may be formed from a rigid material such as a hard plastic and may be adapted to maintain a substantial portion of a residual limb stable while a user is standing or moving. A soft intermediate socket 24 may fit within outer socket 22 to even out pressure in the socket on the residual limb and allow for volume fluctuations of the residual limb. An inner socket, or gel liner, 26 may be placed over the residual limb, to which a portion of suspension device 20 may be secured, as further shown in FIG. 2. Inner socket 26 may be made from a neoprene or nonporous polyurethane. Since inner socket 26 covers the distal end of the residual limb, it may serve to provide protection to the residual limb tissues. Suspension device 20 may provide a user with a convenient way of donning the prosthesis by allowing a user to align the inner socket with the outer socket while the user is seated. Further, the suspension device maintains the relative positioning of the socket assembly components when the user's body weight is insufficient to maintain adequate suspension of the prosthesis from the residual limb, such as during the swing phase of gait when the limb is not weighted.

Suspension device 20 may include a positioning element 28 that may be secured to inner socket 26 using any suitable method, such as screws, or may be integrally formed with inner socket 26, thereby forming an extension of the inner socket. When removably secured, positioning element 28 may be easily exchanged with another positioning element to allow a user to wear different prostheses that require different suspension mechanisms. As shown, the positioning element may be coupled to a distal end of the inner socket.

As shown in FIG. 2, positioning element 28 may include a strap 30 to assist a user in aligning and securing inner socket 26 to outer socket 22. As illustrated, strap 30 may be wider than a string or cable, and therefore easier to maneuver. On at least some of the strap is a gripping portion 32 that may be used to enable maneuvering and securing of the strap relative to other components of the socket assembly. For example, the gripping portion may include teeth 34 or other variations in surface contour that provide a suitable gripping surface. As shown, the gripping portion may have a substantially rectangular cross-section to provide a larger gripping surface than a cable. Further, the gripping portion may be deformable to enable maneuvering and securing of the strap. For example, the gripping portion may be squeezed to restrict movement thereof. Gripping portion 32 may be integrally formed with strap 30 or the gripping portion and strap may be sewn or otherwise secured together. The strap and gripping portion may be made of any sufficiently flexible and durable materials including, but not limited to, textiles and rubbers.

In aligning inner socket 26 with outer socket 22, positioning element 28 may be passed through an opening 36 in intermediate socket 24, which is shown in FIG. 3. Although intermediate socket 24 is typically included in socket assembly 18 to increase the comfort of the prosthesis to a user, it should be appreciated that the presence or absence of the intermediate socket does not affect the functionality of suspension device 20.

As shown in FIGS. 4 and 5, suspension device 20 may include a friction-reducing element 38. The friction-reducing element may facilitate movement of the positioning element from the inner socket to the outer socket. Friction-reducing element 38 may be associated with the outer socket, such as by being provided adjacent an exterior surface of the outer socket, on the distal end of the outer socket, or may be associated with another component of prosthesis 10, such as artificial knee structure 16. Friction-reducing element 38 may be configured to rotate, may be coated to reduce its coefficient of friction, or a combination thereof. For example, friction-reducing element 38 may be a bar or roller 40 that may be coated with polytetrafluoroethylene (Teflon®). Additionally, the shape of friction-reducing element 38, such as cylindrical, may be used to decrease resistance against movement of the positioning element. It should be appreciated that friction-reducing element 38 allows for direction change of positioning element 28 to maintain accessibility and adjustability of the suspension device. Further, the friction-reducing element may be a single unit, as that shown, or may be a system of rollers or pulleys.

As illustrated in FIGS. 4-6, inner socket 26, intermediate socket 24, and outer socket 22 may nestle within each other so that positioning element 28 may be aligned to pass through opening 36 in intermediate socket 24 and to pass through an opening 42 in outer socket 22. Positioning element 28 may be passed under friction-reducing element 38 to facilitate smooth movement of the positioning element as the sockets are aligned. Although the depicted friction-reducing element is shown adjacent to opening 42 in the outer socket, the friction-reducing element may be enclosed within the outer socket, such as by providing a channel in the outer socket into which the friction-reducing element and/or strap may be recessed. In the depicted example, positioning element 28 may be pulled upwards toward the user's torso to guide the inner socket into the outer socket. Suspension device 20 may include a coupling element 44 into which gripping portion 32 may be inserted to selectively restrict movement of the positioning element.

Coupling element 44 may be secured to the outer socket and removably couple the inner socket with the outer socket. The coupling element may receive an extension of the inner socket, such as positioning element 28, and drive the extension through the coupling element. Further, coupling element 44 may selectively restrict movement of the extension, and consequently, movement between the inner socket and the outer socket.

Coupling element 44 may take the form of a ratchet mechanism 46, as depicted in FIGS. 4 and 6. A lever or pawl 48 may provide a mechanical advantage to assist a user in maneuvering positioning element 28, namely gripping portion 32, through the coupling element, thereby aligning the sockets and securing the prosthesis to the user's residual limb. As illustrated in FIG. 6, a user need not directly apply force to the strap to pull the strap taught, but may instead pivot lever 48 to rotate teeth 50 which mate with strap teeth 34. Upon pivoting lever 48, the positioning element may be incrementally forced through the ratchet via the mating relationship between ratchet teeth 50 and strap teeth 34.

It should be appreciated that the ratchet mechanism may reduce the amount of upper body strength required by a user to maneuver and secure the inner socket relative to the outer socket. For example, the ratchet mechanism may provide a mechanical advantage to a user as the user adjusts the positioning element to his or her preferred tension level. Although the ratchet mechanism shown is similar to that used in snowboard bindings, any suitable ratchet mechanism configuration may be used, including, but not limited to, levers, dials, and the like. Additionally, since ratchet teeth 50 may be angled or sloped and thereby permit motion in a single direction, the strap may be prevented from loosening until the user chooses to disengage the ratchet teeth from the gripping portion. As previously noted, the gripping portion may be deformable to accommodate pressure applied by the coupling element to either maneuver or secure the gripping portion.

It should further be appreciated that lever 48 may be used in other configurations. For example, lever 48 may be used to rotate the positioning element around a spool. However, it is preferable that suspension device 20 is close to being flush with the prosthesis so that it is not visible through a user's clothing.

Another illustrative example of a suitable positioning element configuration is depicted in FIG. 7. As shown, positioning element 28 may include a band or elongate strap 52 that at least partially encompasses inner socket 26 and is coupled to gripping portion 32 at one or more locations. For example, band 52 may be a strip of cloth that is secured to opposing sides of the inner socket by a removable fastener 54, such as a hook and loop fastener (e.g., Velcro®), an adhesive (e.g., tape), or the like. Such a configuration may increase user comfort by distributing forces to the more stable lateral tissues of the residual limb, rather than to the distal areas that have been surgically altered. Bands 52 and fastener 54 may be of any suitable widths and thicknesses to provide sufficient strength to withstand the forces necessary to maneuver the inner socket into the outer socket. Additionally, band 52 may be angled or offset relative to the inner socket so that the band does not apply pressure to the distal end of the user's residual limb. Gripping portion 32 may be moveably coupled to the band, such as by including an aperture 56 in the gripping portion through which band 52 passes. A user may therefore select the position of the gripping portion by sliding the gripping portion along the strap or band during alignment of the sockets.

Since the tissues of the residual limb may expand and contract throughout the day, it may also be desirable to provide an easy way to adjust the tension of the strap. Coupling element 44 (see FIGS. 4 and 6) may be located relatively high on outer socket 22, such as near the proximal end thereof, as shown in FIG. 1. In such a configuration, the coupling element is within reach of a user's hand. For instance, a user may access lever 48 through his or her pants pocket, or a hole therein, to adjust the tension of positioning element 28 without having to remove clothing or otherwise interrupt a particular activity. Further, lever 48 may be configured to move to a secured position (shown in FIG. 1) in which movement of the positioning element is restricted and the lever generally conforms to a contour of the outer socket.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where any claim recites "a" or "a first" element or the equivalent thereof, such claim should be understood to include incorporation of one or more such elements, neither requiring nor excluding two or more such elements.

Inventions embodied in various combinations and subcombinations of features, functions, elements, and/or properties may be claimed through presentation of new claims in a related application. Such new claims, whether they are directed to a different invention or directed to the same invention, whether different, broader, narrower or equal in scope to the original claims, are also regarded as included within the subject matter of the inventions of the present disclosure.

What is claimed is:

1. A suspension device for use with a prosthesis having an inner socket and an outer socket, the suspension device comprising:
    a positioning element coupled to the inner socket and adapted to maneuver the inner socket to align the inner socket with the outer socket, the positioning element having a gripping portion with a substantially rectangular cross-section and a varied surface contour; and
    a coupling element mounted to the outer socket and adapted to receive the gripping portion to removably couple the inner socket with the outer socket, wherein the coupling element includes a ratchet mechanism having a lever configured to incrementally drive the gripping portion through the coupling element upon pivoting the lever, thereby restricting movement of the positioning element relative to the outer socket.

2. The suspension device of claim 1, wherein the gripping portion is deformable to accommodate pressure applied by the coupling element.

3. The suspension device of claim 1, wherein the gripping portion includes angled teeth configured to mate with the coupling element.

4. The suspension device of claim 1, wherein the positioning element includes an elongate strap, the gripping portion being selectively positionable along the elongate strap.

5. The suspension device of claim 1, wherein the positioning element is configured to couple to a distal end of the inner socket.

6. The suspension device of claim 1, wherein the positioning element is configured to couple to opposing sides of the inner socket.

7. The suspension device of claim 1, wherein the positioning element is integrally formed with the inner socket.

8. The suspension device of claim 1, wherein the positioning element is configured to pass through an intermediate socket positioned between the inner socket and the outer socket.

9. The suspension device of claim 1, wherein the positioning element is configured to pass from inside the outer socket to outside the outer socket through an opening in a distal end of the outer socket, and the coupling element is mounted to an external surface of the outer socket adjacent a proximal end of the outer socket.

10. The suspension device of claim 9, further comprising a friction reducing element configured to direct the positioning element toward the coupling element, and to reduce friction between the positioning element and the outer socket when selectively securing the positioning element to the coupling element.

11. The suspension device of claim 10, wherein the friction reducing element is positioned adjacent the opening in the distal end of the outer socket.

12. The suspension device of claim 11, wherein the positioning element is configured to pass under the friction reducing element and then upwards alongside the external surface of the outer socket when selectively securing the positioning element to the coupling element.

13. The suspension device of claim 1, wherein the lever is configured to move to a secured position in which movement of the positioning element relative to the coupling element is restricted and the lever generally conforms to a contour of the outer socket.

14. The suspension device of claim 1, wherein the lever includes a plurality of teeth that mate with a plurality of teeth on the gripping portion upon pivoting the lever, thereby driving the extension through the coupling element.

15. The suspension device of claim 1, wherein the coupling element is secured adjacent a proximal end of the outer socket.

16. The suspension device of claim 1, the suspension device further comprising:
    a friction-reducing element configured to direct the positioning element toward the user, the friction-reducing element being adapted to reduce frictional resistance against movement of the positioning element.

17. The suspension device of claim 16, wherein the friction-reducing element is positioned adjacent an exterior surface of the outer socket.

18. The suspension device of claim 17, wherein the friction-reducing element is configured to rotate.

19. The suspension device of claim 17, wherein the friction-reducing element has a lower coefficient of friction than the outer socket.

20. The suspension device of claim 17, wherein the friction-reducing element is substantially cylindrical.

21. The suspension device of claim 17, wherein the friction-reducing element includes one or more pulleys.

* * * * *